US007828737B2

(12) United States Patent
Wakabayashi

(10) Patent No.: US 7,828,737 B2
(45) Date of Patent: Nov. 9, 2010

(54) ACOUSTIC LENS AND ULTRASONIC PROBE USING THE LENS

(75) Inventor: Takashi Wakabayashi, Saitama (JP)

(73) Assignee: Nihon Dempa Kogyo Co., Ltd., Tokyo (JP)

(*) Notice: Subject to any disclaimer, the term of this patent is extended or adjusted under 35 U.S.C. 154(b) by 755 days.

(21) Appl. No.: 11/110,446

(22) Filed: Apr. 20, 2005

(65) Prior Publication Data

US 2005/0245829 A1 Nov. 3, 2005

(30) Foreign Application Priority Data

Apr. 28, 2004 (JP) ............................ 2004-132574

(51) Int. Cl.
*A61B 8/14* (2006.01)

(52) U.S. Cl. ....................... 600/459; 600/472; 310/311; 73/627; 73/642

(58) Field of Classification Search ................ 600/459, 600/437, 472; 310/348–371; 29/594; 73/584, 73/627, 642
See application file for complete search history.

(56) References Cited

U.S. PATENT DOCUMENTS 5,810,009 A * 9/1998 Mine et al. .................. 600/459
2001/0021807 A1* 9/2001 Saito et al. .................. 600/437
2001/0041837 A1* 11/2001 Takeuchi et al. ............ 600/437
2002/0156373 A1* 10/2002 Wakabayashi et al. ...... 600/437
2003/0055339 A1* 3/2003 Fujii et al. .................. 600/459
2004/0206183 A1* 10/2004 Lee et al. ....................... 73/661
2005/0023934 A1* 2/2005 Takeuchi et al. ............ 310/334
2005/0122004 A1* 6/2005 Shibamoto et al. .......... 310/334

FOREIGN PATENT DOCUMENTS

JP 09191497 A * 7/1997
JP HEI9-191497 7/1997

* cited by examiner

*Primary Examiner*—Ruth S Smith
*Assistant Examiner*—Joseph Santos
(74) *Attorney, Agent, or Firm*—Scott D. Wofsy; Edwards Angell Palmer & Dodge LLP

(57) ABSTRACT

The invention has a structure, in an acoustic lens for an ultrasonic probe comprising leg portions which are connected by a planar shape, and a lens portion which is provided on the leg portions and has curvature in the lengthwise direction, wherein the leg portions are made from an attenuation prevention material having the less ultrasonic propagation loss than for the lens portion. Moreover, the leg portions of the acoustic lens are formed with opposite end sides thereof in a bent L-shape. Furthermore, an ultrasonic probe is constructed by adhering onto a piezoelectric element group where a plurality of piezoelectric elements are arranged side by side, an acoustic lens provided with curvature in the lengthwise direction.

3 Claims, 3 Drawing Sheets

ACOUSTIC LENS AND ULTRASONIC PROBE USING THE LENS

BACKGROUND OF THE INVENTION

The present invention relates to an acoustic lens and an ultrasonic probe using the lens, and in particular relates to an acoustic lens in which the ultrasonic propagation loss is minimized.

An ultrasonic probe is used as an ultrasonic echo sounder transducer, for example in medical ultrasonic diagnostic equipment. As one such ultrasonic probe, there is one where piezoelectric elements are arranged in the widthwise direction of the ultrasonic probe and electronic scanned, and further an acoustic lens having curvature in the lengthwise direction is adhered thereto so as to improve the resolution.

FIG. 4 is a transverse cross-sectional view of a conventional example of an ultrasonic probe described below, while FIG. 5 is a longitudinal cross-sectional view thereof.

As shown in FIG. 4 and FIG. 5, the conventional ultrasonic probe comprises; a piezoelectric element group 10, a backing material 20, an acoustic matching layer 30, and an acoustic lens 40. The piezoelectric element group 10 comprises a plurality of piezoelectric elements 10*a* having driving (exciting) electrodes (not shown) on opposite main surfaces, and arranged in the widthwise direction on the backing material 20. The backing material 20 has a damping function, for example, prevents the tailing (ringing) of the occurring ultrasonic vibration.

The acoustic matching layer 30 is provided on the upper surface of the piezoelectric elements 10*a*, and acoustically matches with a specimen (living body). However, the acoustic matching layer 30 becomes unnecessary if the acoustic impedance with the specimen (ore body) is similar.

The acoustic lens 40 is made for example, from silicone rubber in which the acoustic propagation velocity is slower than for the specimen, and comprises, as shown in FIG. 5, a lens portion 40*a*, and leg portions 40*b*. The lens portion 40*a* as shown in FIG. 5, has curvature in the lengthwise direction. The leg portions 40*b* are planar in shape and are formed with the opposite end sides in a bent L-shape. The lens portion 40*a* and the leg portions 40*b* are integrally formed by injecting a silicone rubber into a mold or the like.

The acoustic lens 40 converges the ultrasonic waves radiated from the lengthwise direction of the piezoelectric elements 10*a*, into a beam, so as to improve the resolution in the lengthwise direction. Reference symbol 50 in FIG. 5 denotes synthetic resin filled between the opposite end faces of the piezoelectric element group 10, and the inside of the leg portions 40*b* of the acoustic lens 40 (refer to Japanese Unexamined Patent Publication (TOKKYO KOKAI (Japanese Laid-Open Patent Publication) No. Hei9-191497).

However, such a conventional ultrasonic probe has a problem of desensitization caused by the acoustic lens 40. That is, as shown in FIG. 5, the acoustic lens 40 comprises the lens portion 40*a* having curvature. and the planar leg portions 40*b*. These leg portions 40*b* prevent liquids such as chemicals or the like from entering the acoustic matching layer 30, or the piezoelectric elements 10*a*, from the outside, or facilitate the positioning of other members with respect to the piezoelectric element 10*a*.

Accordingly, the height (thickness) of the acoustic lens 40 is increased due to the thickness of the planar portion of the leg portions 40*b*. On the other hand, the silicone rubber used for the acoustic lens 40 has a large ultrasonic propagation loss. Therefore, due to such a structure, there is a problem of desensitization of the ultrasonic probe as a whole, by increasing the ultrasonic propagation loss due to the acoustic lens 40 over and above what is necessary.

The present invention has an object of providing an acoustic lens with little ultrasonic propagation loss, and an ultrasonic probe using the lens, for which excellent sensitivity is maintained.

SUMMARY OF THE INVENTION

The present invention has a structure, in an acoustic lens for an ultrasonic probe comprising L-shape leg portions connected by a planar portion and a lens portion which is provided on the leg portion and has curvature, wherein the leg portions as made from an attenuation prevention material having less ultrasonic propagation loss than for the lens portion.

According to such a structure, if the acoustic lens of the present invention is applied to an ultrasonic probe, since the ultrasonic propagation loss in the leg portion of the acoustic lens can be minimized, there is the effect of increasing the sensitivity of the ultrasonic probe as a whole.

Moreover, in the present invention, the leg portion of the acoustic lens is formed with opposite end sides thereof in a bent L-shape. Accordingly, it becomes suitable as an acoustic lens for an ultrasonic probe.

Furthermore, in the present invention, an ultrasonic probe is constructed by adhering onto a piezoelectric element group where a plurality of piezoelectric elements are arranged side by side, an acoustic lens comprising the lens portion having curvature in the lengthwise direction of the piezoelectric elements. Accordingly, an ultrasonic probe having little ultrasonic propagation loss and high sensitivity can be obtained.

Moreover, in another embodiment of the present invention, since the piezoelectric elements and the lens portion have the same length, the ultrasonic propagation loss can be further decreased by minimizing the thickness of the lens portion.

DETAILED DESCRIPTION OF THE PREFERRED EMBODIMENTS

Embodiment

Figure 1:
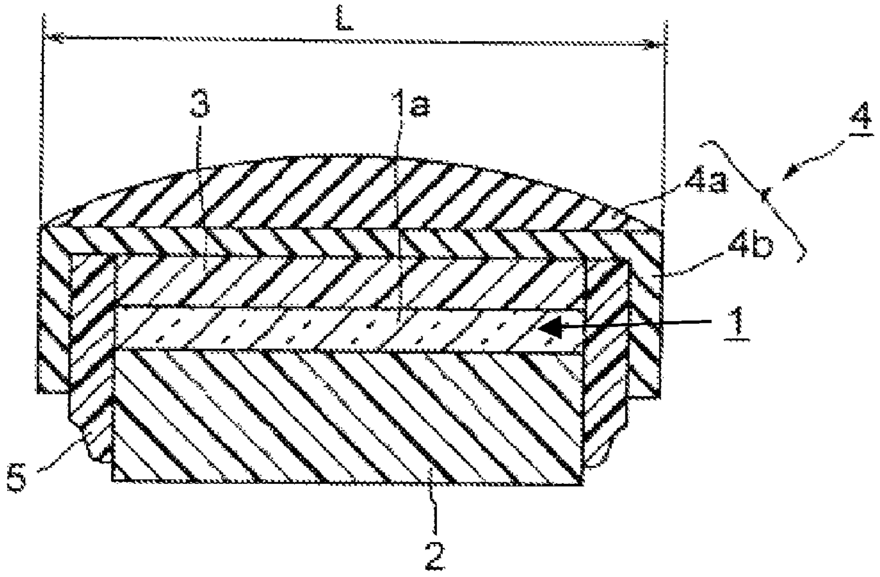
FIG. 1 is a longitudinal (widthwise direction) cross-sectional view showing an embodiment of an ultrasonic probe of the present invention.

FIG. 1 is a longitudinal (lengthwise direction) cross-sectional view explaining an embodiment of an ultrasonic probe of the present invention.

Figure 2:
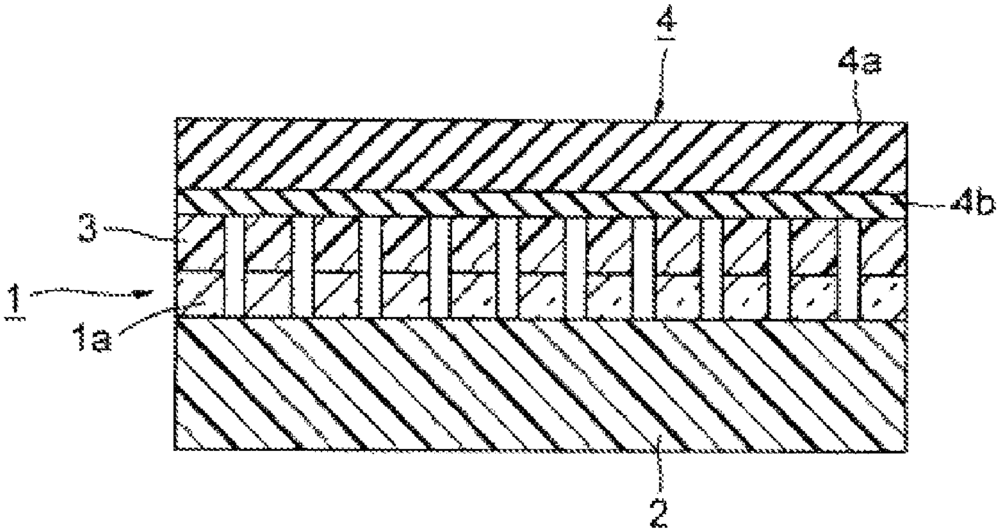
FIG. 2 is a transverse (lengthwise direction) cross-sectional view of the ultrasonic probe shown in FIG. 1.

FIG. 2 is a transverse (widthwise direction) cross-sectional view of the ultrasonic probe shown in FIG. 1.

As shown in FIG. 1 and FIG. 2, the ultrasonic probe of the present invention is constructed by adhering onto a piezoelectric element group 1 which is firmly adhered onto a backing material 2 and has an acoustic matching layer 3 on the front face, an acoustic lens 4 comprising a lens portion 4*a* having curvature formed in the lengthwise direction of the piezoelectric element 1*a*, and bent L-shape leg portions connected by a planar portions 4*b*.

In this embodiment, the lens portion 4*a* of the acoustic lens 4 is formed from silicone rubber, and the leg portion 4*b* is formed from polyimide resin having good attenuation prevention properties. These are formed by adhering the lens portion 4*a* which is made from silicone rubber onto the main surface of the leg portion 4*b* which is made from polyimide resin in a planar shape (film shape), by means of thermo compression bonding or the like.

Moreover, a resin 5 is filled between the end faces of the piezoelectric element group 1, the backing material 2, and the acoustic matching layer 3, and the inside ends of the leg portion 4*b* of the acoustic lens 4.

According to such a structure, the polyimide resin constituting the leg portion 4*b* has considerably less ultrasonic propagation loss than that of the silicone rubber constituting the lens portion 4*a*. Due to this, the ultrasonic attenuation in the leg portion 4*b* is decreased and hence the ultrasonic propagation loss in the acoustic lens 4 can be minimized. Therefore, in the ultrasonic probe of the present invention, the ultrasonic energy can be efficiently propagated, and excellent sensitivity can be maintained.

Moreover, in the ultrasonic probe of the present invention, since the leg portion 4*b* of the acoustic lens 4 is in a bent L-shape, entry of liquid such as a chemical or the like from the side face of the ultrasonic probe can be prevented. In this case, if polyimide resin is used for the leg portion 4*b*, the effect is further increased since polyimide resin has a greater chemical resistance than silicone rubber.

Figure 3:
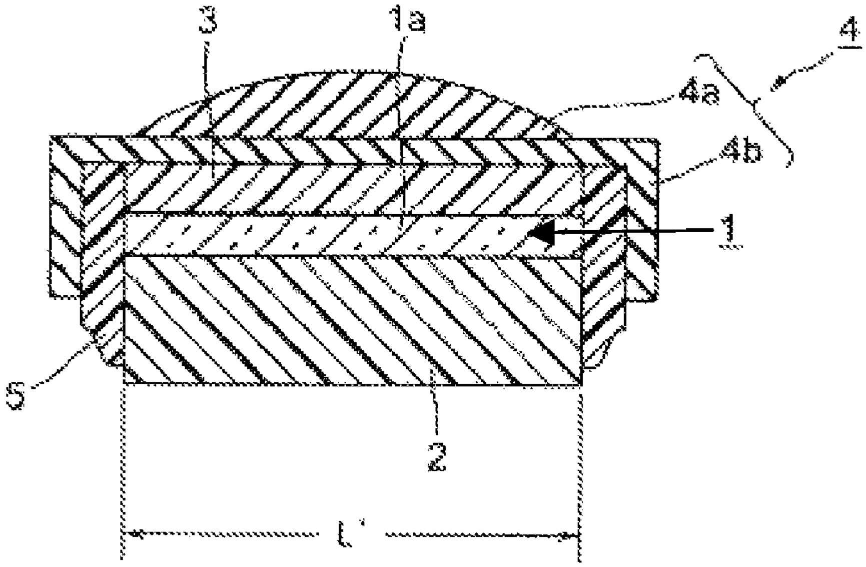
FIG. 3 is a longitudinal cross-sectional view showing another embodiment of the ultrasonic probe of the present invention.
Figure 4:
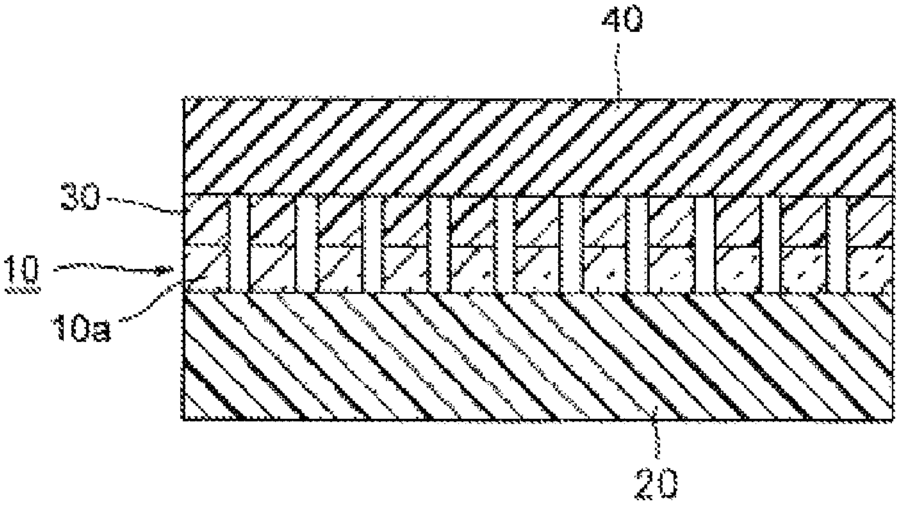
FIG. 4 Prior Art
FIG. 4 is a transverse (lengthwise direction) cross-sectional view of a conventional ultrasonic probe.
Figure 5:
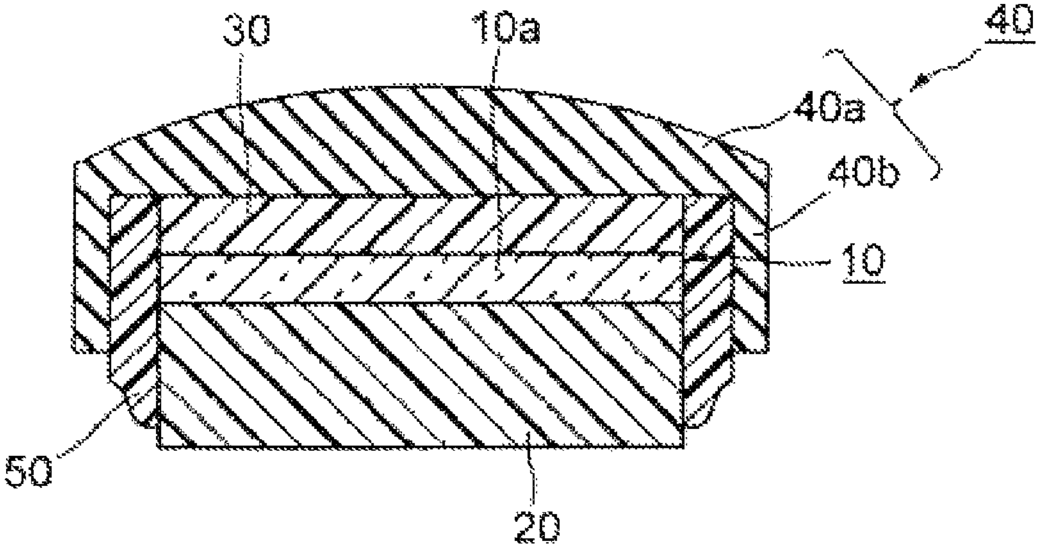
FIG. 5 Prior Art
FIG. 5 is a longitudinal (widthwise direction) cross-sectional view of the conventional ultrasonic probe.

In the above embodiment, as shown in FIG. 1, the length L of the lens portion 4*a* was made greater than that of the piezoelectric element 1*a*. However, for example as shown in FIG. 3, the length L' may be the same as that of the piezoelectric element 1*a*. Accordingly, the thickness of the lens portion 4*a* can be decreased, and hence the ultrasonic propagation loss in the lens portion 4*a* can be further minimized.

Moreover, in the present invention, the leg portion 4*b* formed with a planar shape is made from polyimide resin. However, a similar effect may be demonstrated provided it is made from a resin having less propagation loss than that of the silicone rubber constituting the lens portion 4*a*. Furthermore, the leg portions 4*b* are in a bent L-shape connected by the planar portion, however it may be planar with no bend portion.

What is claimed is:

1. An ultrasonic probe comprising:

a) an acoustic lens adhered onto a piezoelectric element group where a plurality of piezoelectric elements are arranged in a widthwise direction, the acoustic lens including:
   - i) a planar portion with leg portions extending downwardly substantially perpendicularly from opposed ends of the planar portion, wherein the planar portion is configured as a film and is unitary with and of a common material with said leg portions; and
   - ii) a lens portion that has curvature in the lengthwise direction of said piezoelectric elements, said lens portion being adhered directly to the planar portion, wherein said leg and planar portions are made from an attenuation prevention material having less ultrasonic propagation loss than for said lens portion.

2. An ultrasonic probe according to claim 1, wherein said lens portion is made substantially of silicone rubber, and said leg portions are made substantially of polyimide resin.

3. An ultrasonic probe according to claim 1, wherein said piezoelectric elements and said lens portion have the same length in the widthwise direction.

* * * * *